United States Patent
Ueda et al.

(10) Patent No.: US 10,631,764 B2
(45) Date of Patent: Apr. 28, 2020

(54) BREAST MEASUREMENT METHOD AND MEASUREMENT DEVICE

(71) Applicants: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

(72) Inventors: Yukio Ueda, Hamamatsu (JP); Etsuko Yamaki, Hamamatsu (JP); Harumi Sakahara, Hamamatsu (JP); Hiroyuki Ogura, Hamamatsu (JP); Hatsuko Nasu, Hamamatsu (JP); Nobuko Yoshizawa, Hamamatsu (JP)

(73) Assignees: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 707 days.

(21) Appl. No.: 15/310,508

(22) PCT Filed: Apr. 28, 2015

(86) PCT No.: PCT/JP2015/062804
§ 371 (c)(1),
(2) Date: Nov. 11, 2016

(87) PCT Pub. No.: WO2015/174273
PCT Pub. Date: Nov. 19, 2015

(65) Prior Publication Data
US 2017/0119292 A1   May 4, 2017

(30) Foreign Application Priority Data
May 15, 2014   (JP) ................. 2014-101302

(51) Int. Cl.
*A61B 5/00* (2006.01)
*A61B 5/145* (2006.01)
(Continued)

(52) U.S. Cl.
CPC ........ *A61B 5/14546* (2013.01); *A61B 5/1072* (2013.01); *A61B 5/1455* (2013.01);
(Continued)

(58) Field of Classification Search
CPC ... A61B 10/00; A61B 2562/04; A61B 5/1072; A61B 5/14546; A61B 5/1455;
(Continued)

(56) References Cited

U.S. PATENT DOCUMENTS

2004/0039268 A1   2/2004   Barbour et al.
2008/0009748 A1   1/2008   Gratton et al.
(Continued)

FOREIGN PATENT DOCUMENTS

CN   101489471 A   7/2009
EP   2 036 489      3/2009
(Continued)

OTHER PUBLICATIONS

J. S. Choi et al., "US-Guided Optical Tomography: Correlation With Clinicopathologic Variables in Breast Cancer", Ultrasound in Medicine & Biology, vol. 39, No. 2., 2013, pp. 233-240.
(Continued)

*Primary Examiner* — Ruth S Smith
(74) *Attorney, Agent, or Firm* — Faegre Drinker Biddle & Reath LLP

(57) ABSTRACT

A breast measurement apparatus includes a distance measurement unit measuring a distance from a skin to a light absorption portion for a measurement region of a breast which is a normal region including no tumor or an object region including a tumor, a light measurement unit measur-
(Continued)

ing a hemoglobin amount in the measurement region by a light measurement method using measurement light of a predetermined wavelength, a correlation data storage unit storing normal correlation data of the distance to the light absorption portion and a normal hemoglobin amount generated based on measurement results for normal regions, and an evaluation value calculation unit calculating a property evaluation value of the tumor based on the normal hemoglobin amount, obtained from the normal correlation data and the distance to the light absorption portion in the object region, and an object hemoglobin amount in the object region.

14 Claims, 14 Drawing Sheets

(51) Int. Cl.
*A61B 10/00* (2006.01)
*A61B 8/00* (2006.01)
*A61B 5/1455* (2006.01)
*A61B 5/107* (2006.01)
*G16H 50/30* (2018.01)
*A61B 8/08* (2006.01)

(52) U.S. Cl.
CPC ........ *A61B 5/14551* (2013.01); *A61B 5/4312* (2013.01); *A61B 5/7275* (2013.01); *A61B 5/7278* (2013.01); *A61B 8/00* (2013.01); *A61B 8/085* (2013.01); *A61B 8/0825* (2013.01); *A61B 10/00* (2013.01); *G16H 50/30* (2018.01); *A61B 5/708* (2013.01); *A61B 2562/04* (2013.01)

(58) Field of Classification Search
CPC ... A61B 5/14551; A61B 5/4312; A61B 5/708; A61B 5/7275; A61B 5/7278; A61B 8/00; A61B 8/0825; A61B 8/085; G16H 50/30
See application file for complete search history.

(56) References Cited

U.S. PATENT DOCUMENTS

| | | |
|---|---|---|
| 2011/0077523 A1 | 3/2011 | Angott |
| 2011/0137177 A1 | 6/2011 | Toma et al. |

FOREIGN PATENT DOCUMENTS

| | | |
|---|---|---|
| JP | 2001-264245 A | 9/2001 |
| JP | 2005-049238 A | 2/2005 |
| JP | 2009-077931 A | 4/2009 |
| WO | WO-95/02987 A2 | 2/1995 |
| WO | WO-2013/163385 A1 | 10/2013 |
| WO | WO 2014/018728 | 1/2014 |

OTHER PUBLICATIONS

A. Leproux et al., "Assessing tumor contrast in radiographically dense breast tissue using Diffuse Optical Spectroscopic Imaging (DOSI)", Breast Cancer Research, vol. 15 R89, 2013, p. 1-p. 12.
Q. Zhu et al., "Noninvasive Monitoring of Breast Cancer during Neoadjuvant Chemotherapy Using Optical Tomography with Ultrasound Localization", Neoplasia, vol. 10, No. 10, 2008, p. 1028-p. 1040.
International Preliminary Report on Patentability dated Nov. 24, 2016 for PCT/JP2015/062804.

Fig.4
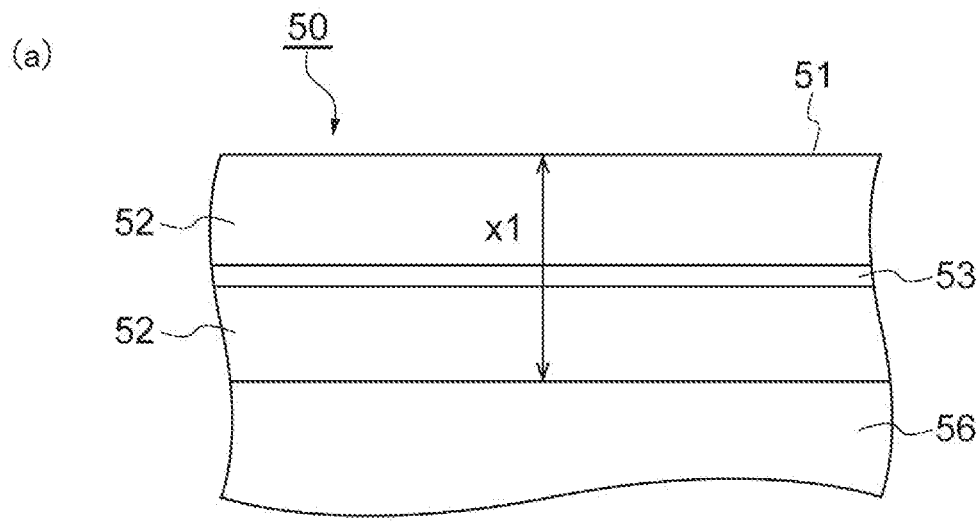
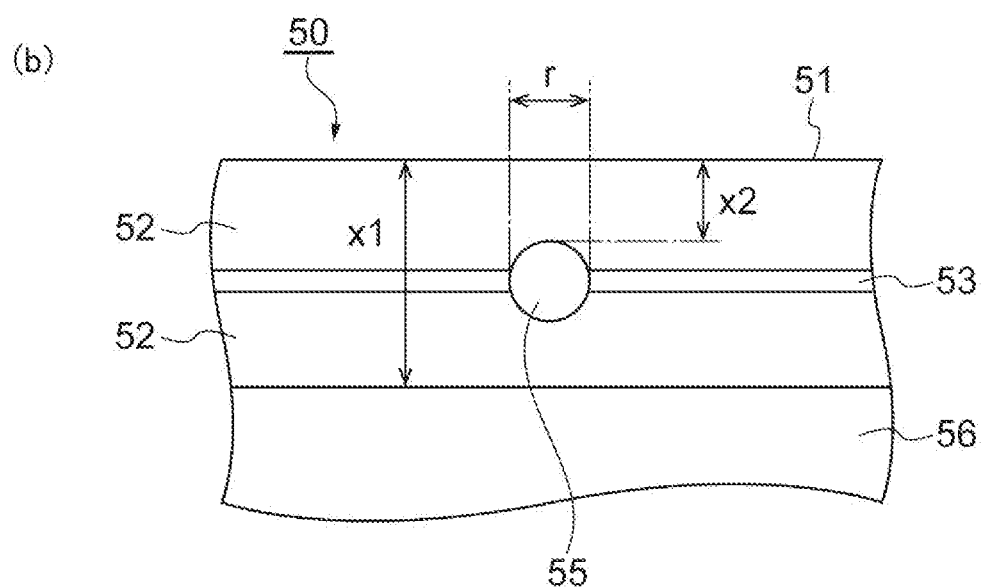

Fig.5
(a)
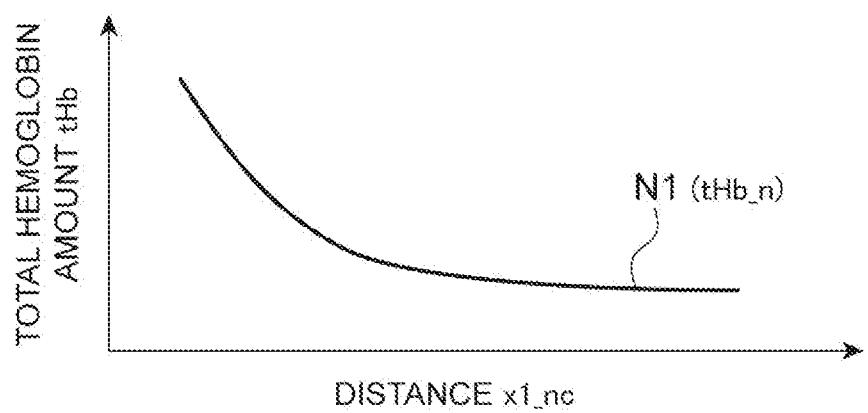
(b)
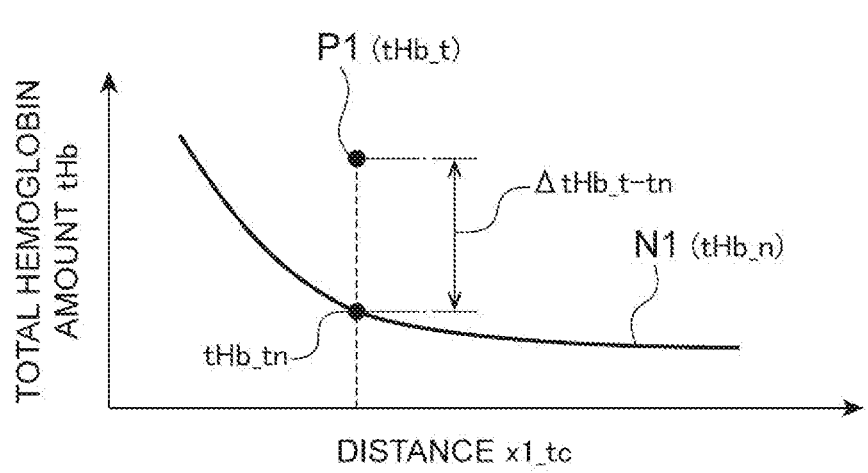

Fig.7
(a)
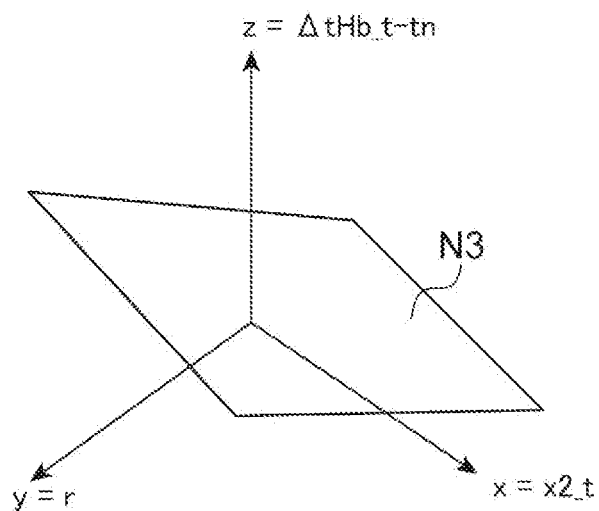
(b)
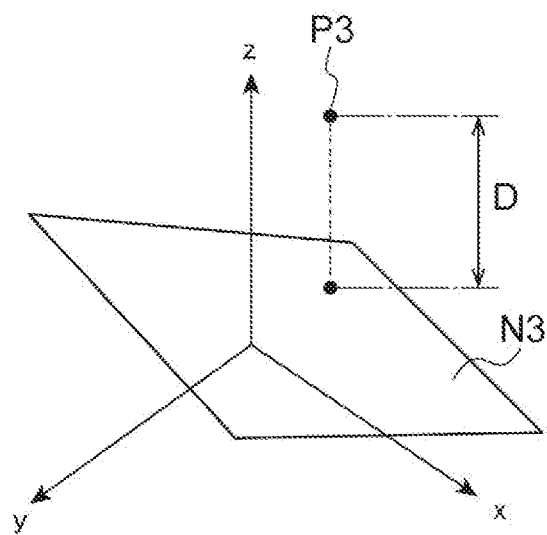

*Fig.8*
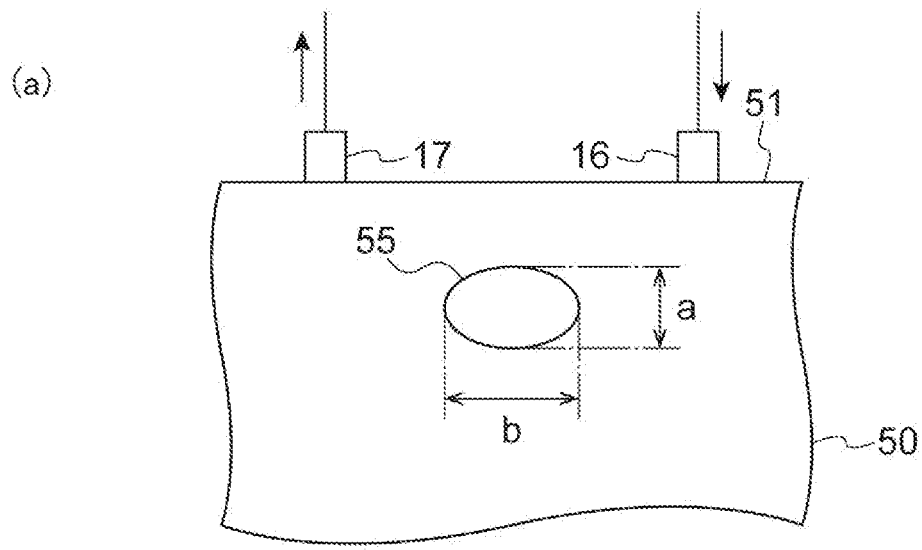
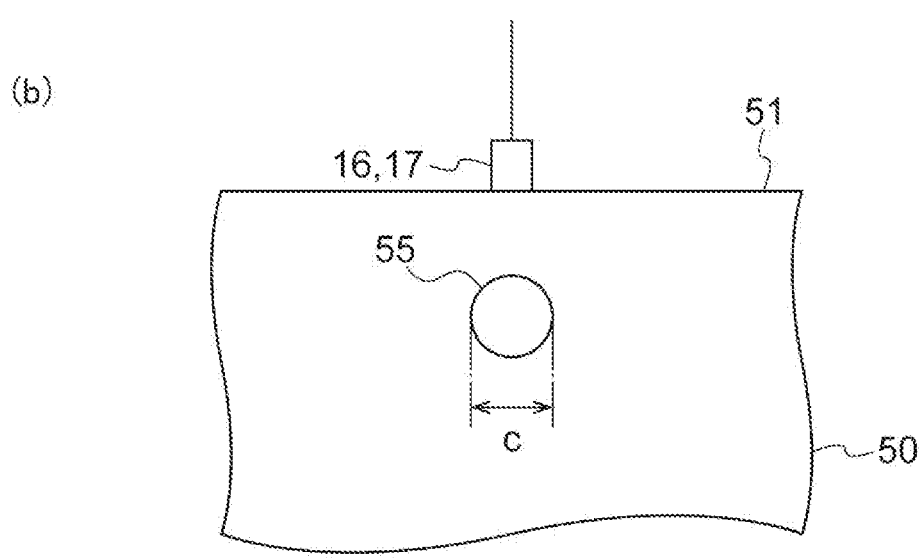

BREAST MEASUREMENT METHOD AND MEASUREMENT DEVICE

TECHNICAL FIELD

The present invention relates to a breast measurement method and a breast measurement apparatus for measuring a property of a tumor inside a breast.

BACKGROUND ART

In recent years, a light measurement method using light with a predetermined wavelength such as near-infrared light has been used for a noninvasive living body measurement such as a breast measurement of breast cancer examination (for example, see Patent Documents 1, 2). In the light measurement method, measurement light of a predetermined wavelength is input through a light input unit into a measurement object region of a subject. Then, the output light propagated inside the measurement object region and output to the outside through a light output unit is detected, and according to the detection result, internal information of the measurement object region is acquired.

In the light measurement method, for example, a hemoglobin amount (oxygenated hemoglobin amount $HbO_2$, deoxygenated hemoglobin amount $Hb$, or total hemoglobin amount $tHb$) in the measurement object region can be acquired as the internal information of the measurement object region. For example, Non Patent Document 1 discloses a method of acquiring a hemoglobin amount by a near-infrared spectroscopic measurement and evaluating a property of a tumor based on the acquired hemoglobin amount.

CITATION LIST

Patent Literature

Patent Document 1: Japanese Patent Application Laid-Open Publication No. 2001-264245
Patent Document 2: Japanese Patent Application Laid-Open Publication No. 2005-049238

Non Patent Literature

Non Patent Document 1: A. Leproux et al., "Assessing tumor contrast in radiographically dense breast tissue using Diffuse Optical Spectroscopic Imaging (DOSI)", Breast Cancer Research Vol. 15 (2013) R89
Non Patent Document 2: J. S. Choi et al., "US-Guided Optical Tomography: Correlation with Clinicopathologic Variables in Breast Cancer", Ultrasound in Medicine and Biology Vol. 39 (2013) pp. 233-240

SUMMARY OF INVENTION

Technical Problem

A breast measurement using the above-described light measurement method is efficient, for example, for measuring and evaluating a property of a tumor in breast cancer examination. The present inventors have studied in detail on such a breast measurement method and measurement accuracy thereof, and as a result, they found that measurement light may be absorbed by a layer of a light absorption portion such as a muscle of a chest wall included deep in a layer of fat or mammary glands of a breast, and that this absorption of the light may lead to deteriorate accuracy of a hemoglobin amount to be acquired by the light measurement method.

In this way, when the measurement accuracy of the hemoglobin amount is deteriorated due to influences of the light absorption portion such as the muscle of the chest wall, the property of the tumor may not be evaluated properly. Further, the influences of the absorption of the measurement light due to the light absorption portion differ depending on a size of the breast, a position of the measurement object region, a measurement angle, and the like, and therefore, it is difficult to find the influences of the light absorption portion with certainty.

The present invention has been made in order to solve the above problem, and an object thereof is to provide a breast measurement method and a breast measurement apparatus capable of improving the measurement accuracy of the property of the tumor inside the breast, regardless of the influences of the light absorption portion such as the muscle of the chest wall and the like.

Solution to Problem

In order to achieve the above object, a breast measurement method according to the present invention is a breast measurement method for measuring a property of a tumor inside a breast of a measurement object, (1) by using a predetermined measurement method of measuring, for a light absorption portion set inside a breast as a distance measurement object, a distance from a skin to the light absorption portion for a measurement region which is a normal region of the breast including no tumor or an object region of the breast including a tumor, and a light measurement method of inputting measurement light into the measurement region through a light input unit, detecting output light output through a light output unit, and measuring a hemoglobin amount in the measurement region, the method including: (2) a correlation data acquisition step of acquiring normal correlation data of the distance to the light absorption portion and a normal hemoglobin amount generated by acquiring the distance to the light absorption portion for each of a plurality of normal regions by the predetermined measurement method and acquiring the normal hemoglobin amount in the normal region by the light measurement method; (3) an object data acquisition step of acquiring the distance to the light absorption portion for the object region by the predetermined measurement method and acquiring an object hemoglobin amount in the object region by the light measurement method; and (4) an evaluation value calculation step of calculating a property evaluation value of the tumor inside the object region based on the normal hemoglobin amount, obtained from the normal correlation data and the distance to the light absorption portion in the object region, and the object hemoglobin amount in the object region.

Further, a breast measurement apparatus according to the present invention is a breast measurement apparatus for measuring a property of a tumor inside a breast of a measurement object, the apparatus including: (a) a distance measurement unit for measuring, for a light absorption portion set inside a breast as a distance measurement object, a distance from a skin to the light absorption portion for a measurement region which is a normal region of the breast including no tumor or an object region of the breast including a tumor by a predetermined measurement method; (b) a light measurement unit, including a light source device for inputting measurement light into the measurement region through a light input unit and a light detection device for detecting output light output from the measurement region through a light output unit, and for measuring a hemoglobin amount in the measurement region by a light measurement method; (c) a correlation data storage unit for storing normal correlation data of the distance to the light absorption portion and a normal hemoglobin amount generated by acquiring the distance to the light absorption portion for each of a plurality of normal regions by the distance measurement unit and acquiring the normal hemoglobin amount in the normal region by the light measurement unit; and (d) an evaluation value calculation unit for calculating a property evaluation value of the tumor inside the object region based on the normal hemoglobin amount, obtained from the normal correlation data and the distance to the light absorption portion in the object region acquired by the distance measurement unit, and an object hemoglobin amount in the object region acquired by the light measurement unit.

In the above-described breast measurement method and breast measurement apparatus, in measuring the property of the tumor inside the breast, in addition to the tumor of the object for measurement and evaluation, a portion which absorbs light in light measurement and influences on measurement results is set as the light absorption portion of the distance measurement object. Further, for the measurement region of the breast which is the normal region including no tumor or the object region including the tumor, the distance from the skin to the light absorption portion is measured by the predetermined distance measurement method, and further, the hemoglobin amount in the measurement region is measured by the light measurement method using measurement light of a predetermined wavelength.

Further, in the above configuration, normal correlation data, generated based on the measurement results for the plurality of normal regions and indicating correlation of the distance to the light absorption portion and the normal hemoglobin amount, is prepared, and further, the object region including the tumor is measured so as to acquire the distance to the light absorption portion and the object hemoglobin amount in the object region. With reference to the measurement data for the plurality of normal regions and the object region, a property evaluation value of the tumor inside the object region is calculated based on an estimate value of the normal hemoglobin amount obtained from the normal correlation data and the distance to the light absorption portion in the object region and the object hemoglobin amount practically measured in the object region.

In this way, according to the configuration of evaluating the measurement result of the hemoglobin amount in the object region including the tumor with reference to the normal correlation data of the distance to the light absorption portion and the hemoglobin amount in the normal region, taking into consideration the distance from the skin to the light absorption portion in the object region and the influences on the measurement result of the hemoglobin amount due to the light absorption portion, it is possible to preferably evaluate the property of the tumor inside the object region. Accordingly, regardless of the influences of the light absorption portion, it is possible to improve measurement accuracy and evaluation accuracy of the property of the tumor inside the breast.

Here, in the breast measurement method and measurement apparatus of the above configuration, the hemoglobin amount in the measurement region acquired by the light measurement method is, for example, a total hemoglobin amount. Alternatively, an oxygenated hemoglobin amount or a deoxygenated hemoglobin amount may be acquired as the hemoglobin amount. In general, at least one of the oxygenated hemoglobin amount, the deoxygenated hemoglobin amount, and the total hemoglobin amount may be acquired as the hemoglobin amount.

Advantageous Effects of Invention

According to a breast measurement method and a breast measurement apparatus of the present invention, it is possible to improve measurement accuracy of a property of a tumor inside a breast regardless of influences of a light absorption portion by the following steps of using a predetermined measurement method for measuring a distance from a skin to a light absorption portion and a light measurement method for measuring a hemoglobin amount in a measurement region for the measurement region of a normal region or an object region of a breast, preparing normal correlation data generated based on measurement results for the normal regions and indicating correlation of the distance to the light absorption portion and a normal hemoglobin amount, measuring the object region including the tumor by the predetermined measurement method and the light measurement method so as to acquire the distance to the light absorption portion in the object region and an object hemoglobin amount, and calculating a property evaluation value of the tumor in the object region based on the normal hemoglobin amount obtained from the normal correlation data and the distance to the light absorption portion in the object region and the object hemoglobin amount in the object region.

BRIEF DESCRIPTION OF DRAWINGS

FIG. 4 includes views illustrating (a) a normal region of a breast including no tumor, and (b) an object region of a breast including a tumor.

FIG. 5 includes (a), (b) views illustrating a first example of a method for evaluating a property of a tumor based on measurement results by the breast measurement apparatus illustrated in FIG. 1.

FIG. 7 includes (a), (b) views illustrating a third example of a method for evaluating a property of a tumor based on measurement results by the breast measurement apparatus illustrated in FIG. 1.

FIG. 8 includes (a), (b) views illustrating an additional evaluation parameter in evaluation of the property of the tumor.

DESCRIPTION OF EMBODIMENTS

Figure 1:
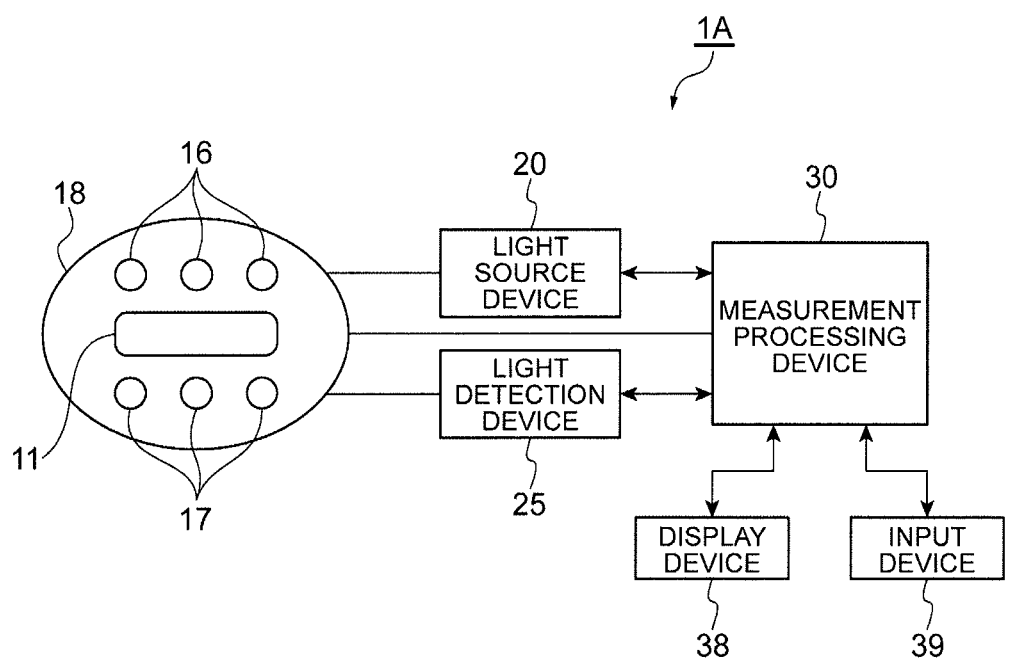
FIG. 1 is a view schematically illustrating a configuration of a breast measurement apparatus according to an embodiment.

Hereinafter, an embodiment of a breast measurement method and a breast measurement apparatus according to the present invention will be described in detail with reference to the accompanying drawings. In the description of the drawings, the same elements will be denoted by the same reference signs, and redundant description will be omitted. The dimensional ratios in the drawings are not always coincident with those in the description.

Figure 2:
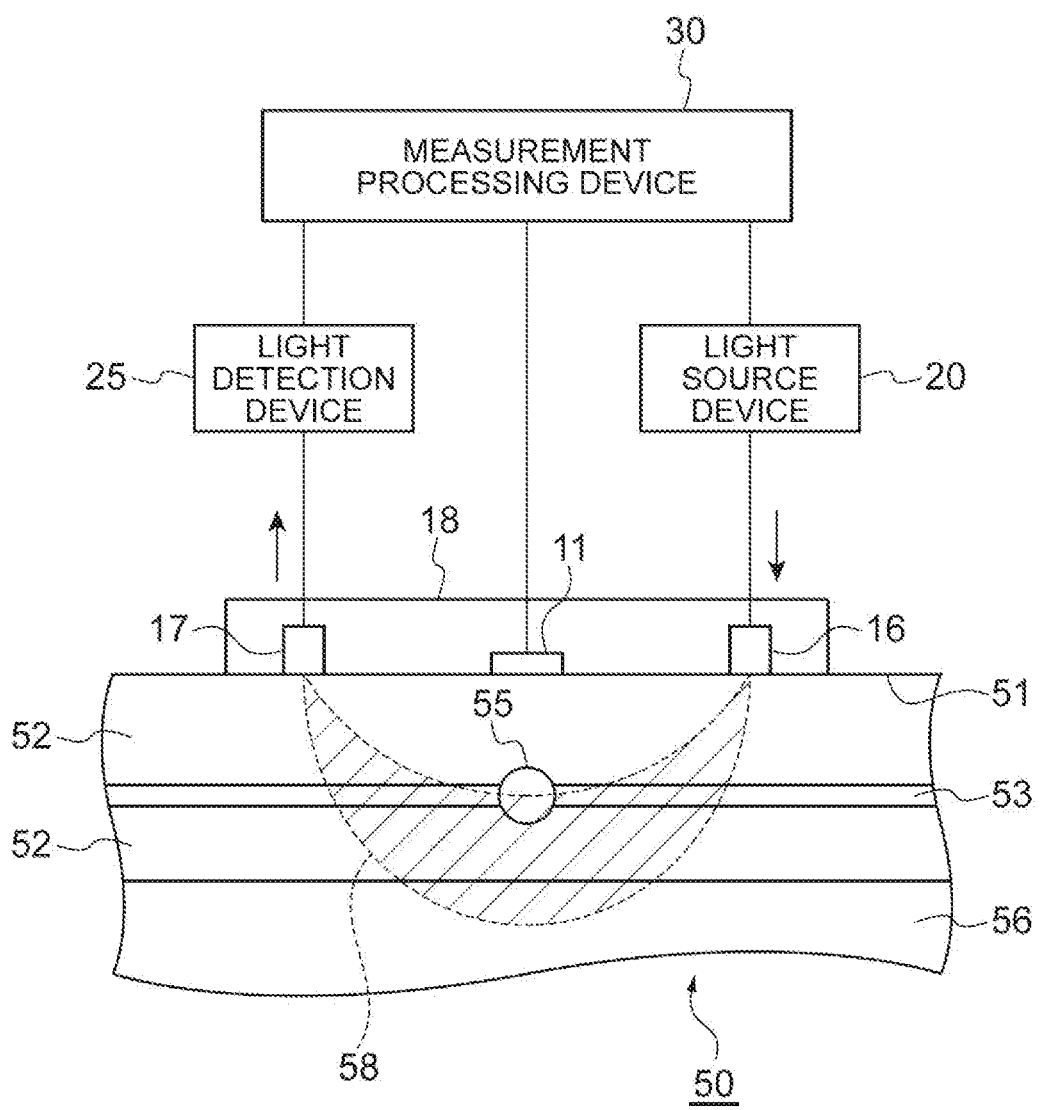
FIG. 2 is a view schematically illustrating ultrasonic measurement and light measurement for a measurement region by the breast measurement apparatus illustrated in FIG. 1.

FIG. 1 is a block diagram schematically illustrating a configuration of a breast measurement apparatus of an embodiment according to the present invention. FIG. 2 is a view schematically illustrating ultrasonic measurement and light measurement carried out for a measurement region by the breast measurement apparatus illustrated in FIG. 1. A breast measurement apparatus 1A according to the present embodiment is a measurement apparatus for measuring a property of a tumor inside a breast of a measurement object. In the measurement using the breast measurement apparatus 1A, as illustrated in FIG. 2, a measurement region 50 is set as a measurement object at a predetermined position of a breast of a subject.

The measurement region 50 is a normal region of the breast including no tumor 55 inside the region or an object region of the breast including the tumor 55 inside the region. The measurement region 50 of the breast includes a skin 51, fat 52, a mammary gland 53, and the like, and the tumor 55 of the object for measurement and evaluation is typically located at the position on the mammary gland 53. Seen from the skin 51, at a position farther (deeper) than the fat 52, mammary gland 53, and the like, there is a portion such as a muscle of a chest wall or the like which greatly absorbs light. Hereinafter, the portion such as the muscle of the chest wall or the like will be referred to as a light absorption portion 56. As described later, the light absorption portion 56 is set as a measurement object of distance in measurement carried out by the breast measurement apparatus 1A.

Figure 3:
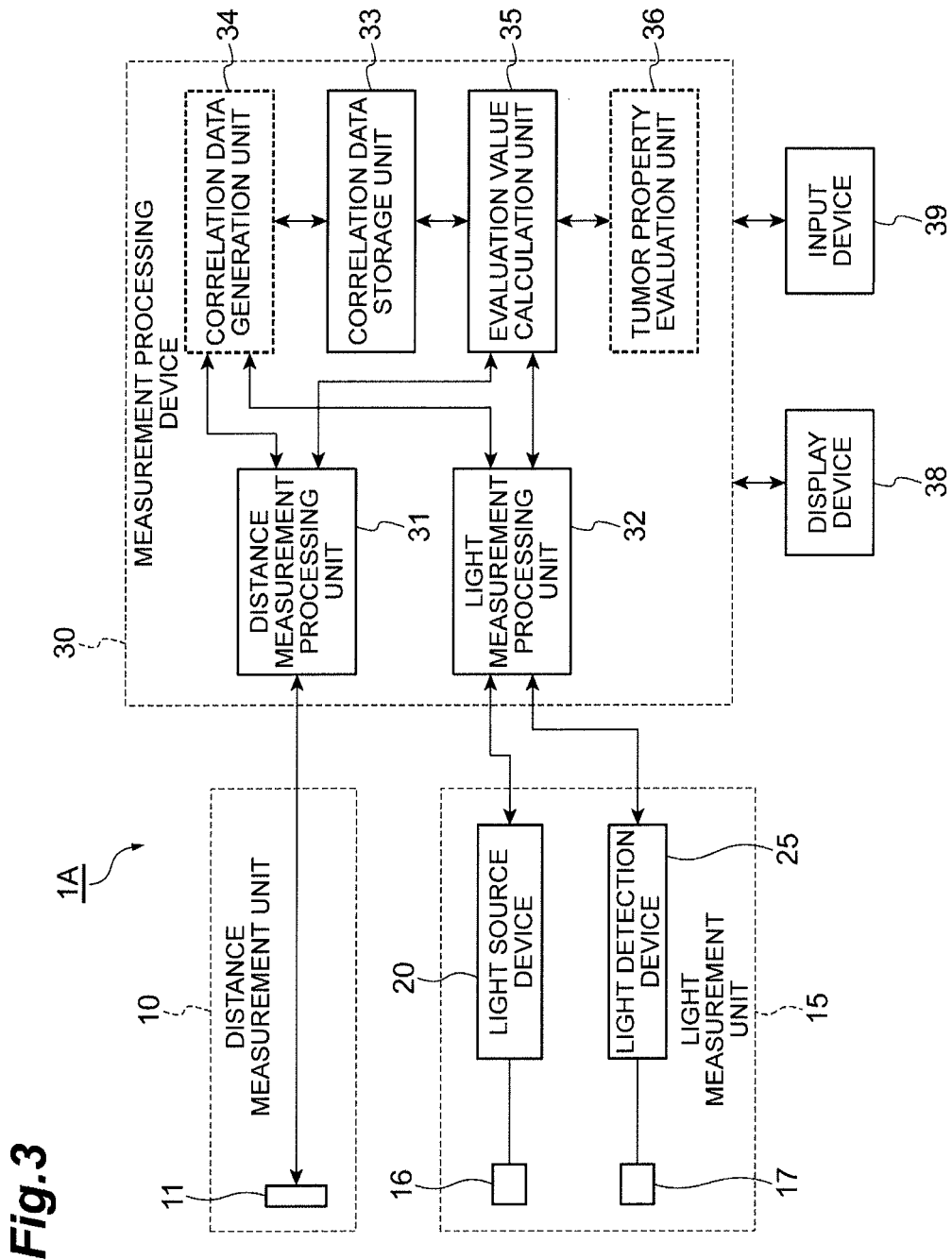
FIG. 3 is a block diagram illustrating an example of a specific configuration of a measurement processing device in the breast measurement apparatus illustrated in FIG. 1.
Figure 14:
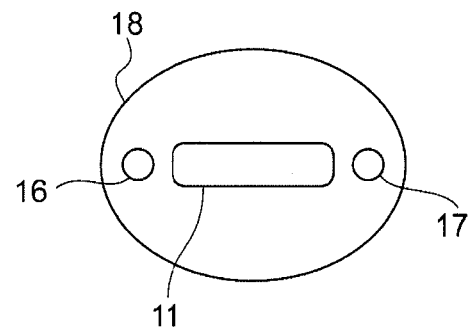
FIG. 14 is a view illustrating a modification example of a measurement probe.

The breast measurement apparatus 1A includes a distance measurement unit 10 (See FIG. 3), a light measurement unit 15 (See FIG. 3), a measurement probe 18 (See FIGS. 1, 2, and 14), and a measurement processing device 30 (See FIGS. 1, 2, and 3). The measurement probe 18 is configured to integrally hold an ultrasonic measurement unit (ultrasonic probe) 11 included in the distance measurement unit 10, and a light input unit (light input probe) 16 and a light output unit (light output probe) 17 included in the light measurement unit 15. The measurement for the measurement region 50 of the subject by the present measurement device 1A is carried out in a state where this measurement probe 18 is applied on the measurement region 50 as illustrated in FIG. 2. Here, arrangements and positional relationships of the ultrasonic measurement unit 11, the light input unit 16, and the light output unit 17 in the measurement probe 18 are properly set in accordance with a specific measurement content and the like.

The distance measurement unit 10 is distance measurement means which measures, for the above-described light absorption portion 56 set as the distance measurement object, a distance (depth) from the skin 51 to the light absorption portion 56 by a predetermined measurement method (distance measurement method) for the measurement region 50 of the breast which is the normal region with no tumor 55 to be evaluated or the object region with the tumor 55. In the present embodiment, an ultrasonic measurement method is used as a method for measuring the distance to the light absorption portion 56.

The distance measurement unit 10 by the ultrasonic measurement method includes the ultrasonic measurement unit 11. The ultrasonic measurement unit 11 specifically includes, for example, an acoustic lens, a matching layer, a transducer, and a damper in order from an end portion in contact with the measurement region 50. The ultrasonic measurement unit 11 transmits ultrasonic wave to the measurement region 50 by a transmitter, and receives reflected ultrasonic wave by a receiver so as to acquire ultrasonic measurement data (for example, ultrasonic image data) of the measurement region 50. The measurement data acquired by the ultrasonic measurement unit 11 is sent out to the measurement processing device 30 as an ultrasonic measurement signal.

The light measurement unit 15 is light measurement means which measures a hemoglobin amount in the measurement region 50 by using measurement light having a predetermined wavelength (for example, near-infrared light) by a light measurement method in which the measurement light is input into the measurement region 50 through the light input unit 16 so as to detect output light output through the light output unit 17. In the present embodiment, a time resolved spectroscopy (TRS) method is specifically used as the light measurement method, which is a method using a time-resolved waveform of detection light with pulse light. Hereinafter, the hemoglobin amount in the measurement region 50 acquired by the light measurement method will be mainly described as a total hemoglobin amount tHb. Further, regarding acquisition of the hemoglobin amount by the light measurement method, Patent Document 2 may be referred to as an example.

The light measurement unit 15 by the TRS method includes the light input unit 16 used for inputting the light into the measurement region 50, the light output unit 17 used for outputting the light from the measurement region 50, a light source device 20, and a light detection device 25. The light source device 20 supplies pulse measurement light with a predetermined wavelength and inputs the pulse measurement light into the measurement region 50 through the light input unit 16. The light detection device 25 detects the output light output from the measurement region 50 through the light output unit 17 and sends out the acquired detection data to the measurement processing device 30 as a light measurement signal.

The output light detected by the light detection device 25 is, for example, as a propagation path of the measurement light inside the measurement region 50 schematically illustrated in FIG. 2 by an area 58, the measurement light which is input from the light input unit 16 and is propagated through the measurement region 50 as being absorbed or scattered and then reaches the light output unit 17. Further, the light source device 20 and the light input unit 16 as well as the light detection device 25 and the light output unit 17 are respectively optically coupled through an optical system such as an optical fiber or the like.

Regarding a specific configuration of the light measurement unit 15, the light source device 20 is, for example, a semiconductor picosecond pulse laser light source including a laser diode and a driving circuit. The laser diode is stably lightened up by the driving circuit and supplies as the measurement light the near-infrared light with three wavelength bands of wavelengths of 760 nm, 800 nm, and 830 nm. Further, the light source device 20 is not limited to the laser diode, and for example, a solid-state laser light source or a light emitting diode (LED) may be used, or a configuration combining a wavelength selection filter with a super luminescent diode (SLD), a lamp-type light source or the like may also be used.

The light detection device 25 includes, for example, a photomultiplier tube having high sensitivity characteristic for light with a wavelength band of the near-infrared light, and an amplifier. Further, by providing the wavelength selection filter, the light detection device 25 may also be configured to reduce influences of light other than the near-infrared light supplied from the light source device 20. The light detection device 25 is not limited to the photomultiplier tube, and for example, a semiconductor photodetector such as an avalanche photodiode may be used. Here, FIG. 1 illustrates three light input units 16 and light output units 17 in the measurement probe 18, in accordance with the configuration where the near-infrared light with the three wavelength bands is used as the measurement light as described above.

The ultrasonic measurement signal output from the ultrasonic measurement unit 11 of the distance measurement unit 10 and the light measurement signal output from the light detection device 25 of the light measurement unit 15 are respectively input to the measurement processing device 30. The measurement processing device 30 is measurement processing means which controls measurement operations by the distance measurement unit 10 and the light measurement unit 15, and performs necessary data processing, analysis, and the like for the measurement signals input from the distance measurement unit 10 and the light measurement unit 15.

The measurement processing device 30 includes, for example, a computer. Further, a display device 38, which is used for displaying, to an operator, information regarding the breast measurement such as information of measurement conditions and measurement results in the breast measurement apparatus 1A, and an input device 39, which is used for the operator to input information, instructions, and the like necessary for the breast measurement, are coupled to the measurement processing device 30.

FIG. 3 is a block diagram illustrating an example of a specific configuration of the measurement processing device 30 in the breast measurement apparatus 1A illustrated in FIG. 1. The measurement processing device 30 according to the present embodiment is configured to include a distance measurement processing unit 31, a light measurement processing unit 32, a correlation data storage unit 33, a correlation data generation unit 34, an evaluation value calculation unit 35, and a tumor property evaluation unit 36.

The distance measurement processing unit 31 performs data processing for the ultrasonic measurement signal input from the distance measurement unit 10 so as to acquire the distance from the skin 51 to the light absorption portion 56 in the measurement region 50. In the configuration using the ultrasonic measurement method in the distance measurement unit 10, the ultrasonic image data, which is possible to observe, for example, conditions of tissues under the skin in the measurement region 50 of the subject, is acquired as the measurement data.

In the distance measurement processing unit 31, for example, an ultrasonic image acquired as the measurement result by the distance measurement unit 10 is displayed on the display device 38, and the distance to the light absorption portion 56 is acquired by the information input from the input device 39 as a result which is determined by the operator based on the ultrasonic image. Further, the distance measurement processing unit 31 may perform image processing and analysis with predetermined algorithm for the ultrasonic image so as to automatically acquire the distance to the light absorption portion 56.

The light measurement processing unit 32 performs data processing for the light measurement signal input from the light measurement unit 15 so as to acquire the hemoglobin amount in the measurement region 50. In the configuration using the TRS method in the light measurement unit 15, a time-resolved response waveform with respect to the pulse measurement light is acquired by time-resolved measurement using a time-correlated single photon counting method, and the hemoglobin amount such as the total hemoglobin amount is calculated based on the time-resolved response waveform.

The correlation data storage unit 33 is correlation data storage means which stores normal correlation data of the distance from the skin 51 to the light absorption portion 56 in the normal region of the breast including no tumor 55 and a normal hemoglobin amount which is the hemoglobin amount in the normal region (correlation data acquisition step). The normal correlation data stored in the correlation data storage unit 33 is correlation data generated by acquiring, for each of the plurality of normal regions, the distance to the light absorption portion 56 by the distance measurement unit 10 and acquiring the normal hemoglobin amount in the normal region by the light measurement unit 15.

Regarding the plurality of normal regions which are measurement objects for generating the normal correlation data, specifically, for example, one normal region may be set on each of a plurality of subjects, or a plurality of normal regions may be set on one subject, or a plurality of normal regions may be set on each of a plurality of subjects. In the configuration example illustrated in FIG. 3, the correlation data storage unit 33 is provided with the correlation data generation unit 34 for generating the normal correlation data based on the measurement results by the distance measurement unit 10 and the light measurement unit 15. Here, for example, in the case where the normal correlation data is generated in advance and is stored in the correlation data storage unit 33, the correlation data generation unit 34 is not necessary.

Further, the object region of the breast including the tumor 55 which is to be measured and evaluated by the breast measurement apparatus 1A is also measured as similar to the above-described normal region. Accordingly, the distance from the skin 51 to the light absorption portion 56 in the object region is acquired by the distance measurement unit 10 and the distance measurement processing unit 31. Further, an object hemoglobin amount which is the hemoglobin amount in the object region is acquired by the light measurement unit 15 and the light measurement processing unit 32 (object data acquisition step).

The evaluation value calculation unit 35 is evaluation value calculation means which calculates a property evaluation value of the tumor 55 inside the object region. Specifically, the evaluation value calculation unit 35 acquires the normal correlation data from the correlation data storage unit 33 (correlation data acquisition step). Further, the distance to the light absorption portion 56 measured in the object region is acquired from the distance measurement processing unit 31, and the object hemoglobin amount measured in the object region is acquired from the light measurement processing unit 32. Then, the evaluation value calculation unit 35 calculates the property evaluation value of the tumor 55 based on the normal hemoglobin amount (an estimate value of the normal hemoglobin amount), obtained from the normal correlation data and the distance to the light absorption portion 56 in the object region, and the object hemoglobin amount in the object region (evaluation value calculation step).

Further, in the configuration example illustrated in FIG. 3, the tumor property evaluation unit 36 is provided for the evaluation value calculation unit 35. The tumor property evaluation unit 36 performs necessary evaluation for the property of the tumor 55 in the object region with reference to the property evaluation value calculated in the evaluation value calculation unit 35. Examples of the property of the tumor 55 to be evaluated include Ki-67, HER2, ER, PGR, nuclear grade, histological grade, lymph node metastasis, histological classification, and the like. Here, the tumor property evaluation unit 36 may not be provided if not necessary. Further, in addition to the correlation data storage unit 33, the measurement processing device 30 may also be provided with a storage unit which stores measurement data such as the measurement results by the distance measurement unit 10 and the light measurement unit 15, the property evaluation value calculated by the evaluation value calculation unit 35, and the like.

Effects of the breast measurement apparatus 1A according to the embodiment and the breast measurement method by the apparatus will be described.

In the breast measurement apparatus 1A illustrated in FIG. 1 to FIG. 3 and the breast measurement method, in measuring the property of the tumor 55 inside the breast of the subject, in addition to the tumor 55 of the object for measurement and evaluation, a portion which absorbs light in the light measurement and influences on the measurement results is set as the light absorption portion 56 of the distance measurement object. Further, for the measurement region 50 of the breast which is the normal region including no tumor 55 or the object region including the tumor 55, the distance from the skin 51 to the light absorption portion 56 is measured by the distance measurement unit 10 with the predetermined distance measurement method, and further, the hemoglobin amount in the measurement region is measured by the light measurement unit 15 with the light measurement method using the measurement light of the predetermined wavelength.

Further, in the above configuration, the normal correlation data, generated based on the measurement results for the plurality of normal regions and indicating correlation of the distance to the light absorption portion 56 and the normal hemoglobin amount is prepared and stored in the correlation data storage unit 33, and further, the object region including the tumor 55 is measured so as to acquire the distance to the light absorption portion 56 and the object hemoglobin amount in the object region. With reference to the measurement data for the plurality of normal regions and the object region, the property evaluation value of the tumor 55 inside the object region is calculated based on the estimate value of the normal hemoglobin amount obtained from the normal correlation data and the distance to the light absorption portion 56 in the object region and the object hemoglobin amount practically measured in the object region.

Here, as described above, in measuring the property of the tumor 55 inside the breast by using the light measurement method, the presence of the light absorption portion 56 such as the muscle of the chest wall positioned deeply of a layer of the fat 52 or mammary gland 53 in the breast may be a problem. That is, in the light measurement method, the hemoglobin amount in the measurement region 50 including the tumor 55 is measured so as to evaluate the property of the tumor such as a condition of the tumor 55. However, when the distance from the skin 51 to the light absorption portion 56 is small in the measurement region 50, a part of the measurement light propagated through the measurement region 50 reaches the light absorption portion 56, for example as illustrated with the propagation path area 58 of the measurement light in FIG. 2.

In this way, when the measurement light reaches the light absorption portion 56 such as the muscle of the chest wall, the hemoglobin amount obtained from the measurement result by the light measurement method may be overestimated due to large absorption of the near-infrared measurement light in the light absorption portion 56. Therefore, in evaluating the property of the tumor, it is difficult to evaluate the tumor with a correct hemoglobin amount.

In contrast, as described above, according to the configuration of evaluating the measurement result of the hemoglobin amount in the object region including the tumor 55 with reference to the normal correlation data of the distance to the light absorption portion 56 in the normal region and the hemoglobin amount, it is possible to preferably evaluate the property of the tumor 55 inside the object region, as taking into consideration the distance from the skin 51 to the light absorption portion 56 in the object region and the influences on the measurement result of the hemoglobin amount due to the light absorption portion 56. Accordingly, regardless of the influences of the light absorption portion 56, it is possible to improve measurement accuracy and evaluation accuracy of the property of the tumor 55 inside the breast.

Here, in the breast measurement apparatus 1A of the above configuration and the breast measurement method, the hemoglobin amount in the measurement region acquired by the light measurement unit 15 with the light measurement method using the near-infrared light or the like is, for example, a total hemoglobin amount. Alternatively, an oxygenated hemoglobin amount or a deoxygenated hemoglobin amount may be acquired as the hemoglobin amount. In general, at least one of the oxygenated hemoglobin amount, the deoxygenated hemoglobin amount, and the total hemoglobin amount may be acquired as the hemoglobin amount.

Specific examples of the light absorption portion 56 in the measurement region 50, which is to be taken into consideration in the light measurement, include the muscle of the chest wall as described above. Examples of the muscle of the chest wall include pectoralis major muscles and chest wall muscles such as external intercostal muscles, internal intercostal muscles, subcostal muscles, levatores costarum longi muscles, levatores costarum breves muscles, transverse thoracic muscles, and also include ribs. In the case where the muscle of the chest wall is thin, it is necessary to consider a lung located deeper than the muscle of the chest wall as the light absorption portion 56 which absorbs light.

Regarding the light absorption portion 56 which absorbs the measurement light of the predetermined wavelength at a certain level or more and influences on the measurement result in the light measurement inside the breast, in general, the portion is preferably a muscle of a chest wall, a rib, a mammary gland, or a lung. It is possible to preferably improve the measurement accuracy of the property of the tumor 55 inside the breast by taking into consideration the influences on the measurement result of the light absorption in these portions. The light absorption portion 56 is preferably properly set as taking into consideration a light absorption property and the like inside the breast or the vicinal portion thereof.

Further, regarding the measurement method used for measuring the distance to the light absorption portion 56 in the distance measurement unit 10, as described above, it is preferable to apply the ultrasonic measurement method of acquiring the ultrasonic measurement data of the measurement region 50 by transmitting the ultrasonic wave to the measurement region 50 and receiving the reflected ultrasonic wave. In this way, by applying the ultrasonic measurement method as a method for measuring the distance from the skin 51 to the light absorption portion 56 in the measurement region 50, the distance to the light absorption portion 56 can be preferably measured.

Regarding the property evaluation value of the tumor 55, specifically, the evaluation value calculation unit 35 may be configured to calculate a difference value between the estimate value of the normal hemoglobin amount and the object hemoglobin amount obtained for the object region as the property evaluation value. Further, the evaluation value calculation unit 35 may be configured to calculate a corrected evaluation value obtained by correcting the object hemoglobin amount based on the estimate value of the normal hemoglobin amount obtained for the object region as the property evaluation value.

In this way, according to the configuration using the difference value of the hemoglobin amount or the evaluation value after correcting the hemoglobin amount as the property evaluation value of the tumor 55 in the object region, it is possible to preferably evaluate and determine the property of the tumor 55 based on the measurement result.

Further, regarding the property evaluation value of the tumor 55, the correlation data storage unit 33 may be configured to prepare hemoglobin amount correction data generated based on correlation of the distance to the light absorption portion 56 and the normal hemoglobin amount as the normal correlation data, and the evaluation value calculation unit 35 may be configured to calculate the corrected evaluation value in which the object hemoglobin amount is corrected based on a correction value obtained from the hemoglobin amount correction data and the distance to the light absorption portion in the object region as the property evaluation value.

In this way, according to the configuration in which the hemoglobin amount correction data used for correcting the object hemoglobin amount is prepared as the normal correlation data, it is possible to preferably evaluate and determine the property of the tumor 55 based on the measurement result.

Regarding evaluation of the property of the tumor 55, the evaluation value calculation unit 35 may be configured to acquire a single or a plurality of evaluation parameters for the tumor 55 in addition to the above-described property evaluation value, and evaluate the property of the tumor 55 based on the property evaluation value and the single or the plurality of evaluation parameters. According to this configuration, it is possible to further improve the measurement accuracy of the property of the tumor 55 inside the breast.

The measurement and evaluation method of the property of the tumor 55 inside the breast by the breast measurement apparatus 1A illustrated in FIG. 1 to FIG. 3 will be further described in more detail. FIG. 4 includes views illustrating (a) a normal region of a breast including no tumor 55, and (b) an object region of a breast including the tumor 55. Hereinafter, as illustrated in (a) and (b) in FIG. 4, the distance from the skin 51 to the light absorption portion 56 in the measurement region 50 is referred to as x1, the distance from the skin 51 to a surface of the tumor 55 is referred to as x2, and a diameter of the tumor 55 is referred to as r.

Regarding abbreviations hereinafter used in indicating each parameter, "n" is an abbreviation of "normal" indicating the normal region, "t" is an abbreviation of "tumor" indicating the object region with the tumor, "c" is an abbreviation of "chest wall" indicating the light absorption portion such as the muscle of the chest wall and the like, and "p" is an abbreviation of "patient" indicating the subject. In examples hereinafter described, the hemoglobin amount in the measurement region 50 is mainly assumed to be the total hemoglobin amount tHb.

(a) and (b) in FIG. 5 are views illustrating a first example of the method for evaluating a property of a tumor 55 based on measurement results obtained by the breast measurement apparatus 1A illustrated in FIG. 1 to FIG. 3. In the present example, first, the distance measurement unit 10 measures a distance $x1\_nc$ from a skin 51 to a light absorption portion 56 for a normal region with no tumor 55. Further, the light measurement unit 15 measures a normal hemoglobin amount $tHb\_n$ which is a total hemoglobin amount in the normal region. This measurement is carried out on normal regions set at a plurality of positions for a plurality of subjects.

Next, normal correlation data of the distance $x1\_nc$ to the light absorption portion 56 and the normal hemoglobin amount $tHb\_n$ for the normal region is generated with reference to measurement data obtained for the plurality of normal regions, as illustrated by a graph N1 in (a) in FIG. 5. This normal correlation data may be prepared as an approximation formula such as the following Formula (1).

$$tHb = a1 \times x1^3 + b1 \times x1^2 + c1 \times x1 + d1 \qquad (1)$$

Alternatively, the normal correlation data may be prepared as a correlation table. Further, as described later, a plurality of normal correlation data may be prepared in accordance with attributes of the normal regions.

Subsequently, the distance measurement unit 10 measures a distance $x1\_tc$ from the skin 51 to the light absorption portion 56 for an object region with the tumor 55 from a position right above the tumor 55. Further, the light measurement unit 15 measures an object hemoglobin amount $tHb\_t$ which is the total hemoglobin amount in the object region from the position right above the tumor 55. (b) in FIG. 5 indicates a measurement data point P1 obtained from the measurement result for the object region as well as the graph N1 of the normal correlation data.

After completing the measurement of the object region, the distance $x1\_tc$ to the light absorption portion 56 in the object region is substituted into the Formula (1) of the normal correlation data so as to obtain an estimate value $tHb\_tn$ of the normal hemoglobin amount for the object region represented by the following Formula (2).

$$tHb\_tn = a1 \times (x1\_tc)^3 + b1 \times (x1\_tc)^2 + c1 \times (x1\_tc) + d1 \qquad (2)$$

Then, a difference value $\Delta tHb\_t-tn$ between the estimate value $tHb\_tn$ of the normal hemoglobin amount and the measured object hemoglobin amount $tHb\_t$ is calculated as a property evaluation value of the tumor 55 in the object region by the following Formula (3).

$$\Delta tHb\_t-tn = tHb\_t - tHb\_tn \quad (3)$$
$$= tHb\_t - \begin{Bmatrix} a1 \times (x1\_tc)^3 + \\ b1 \times (x1\_tc)^2 + \\ c1 \times (x1\_tc) + d1 \end{Bmatrix}$$

The difference value ΔtHb_t–tn of the hemoglobin amount obtained in this way indicates the total hemoglobin amount in which the influences of the light absorption portion 56 such as the muscle of the chest wall in the object region are reduced. Therefore, it is possible to exactly evaluate the tumor 55 in the object region by evaluating the property of the tumor with the difference value ΔtHb_t–tn as the property evaluation value. In this example, the difference value of the hemoglobin amount is obtained as the property evaluation value of the tumor, but it is not limited to such a configuration, and for example, a value of a ratio of the hemoglobin amount may also be used as the property evaluation value.

Figure 6:
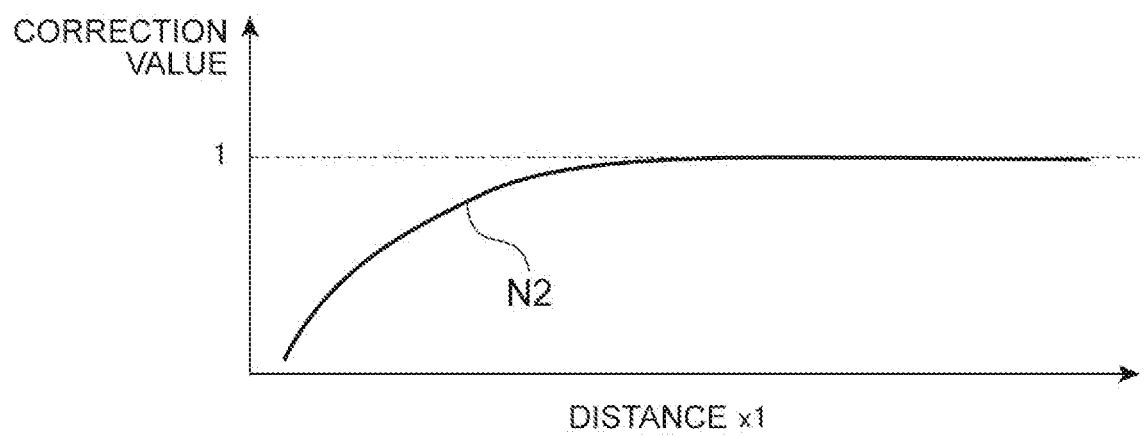
FIG. 6 is a view illustrating a second example of a method for evaluating a property of a tumor based on measurement results by the breast measurement apparatus illustrated in FIG. 1.

FIG. 6 is a view illustrating a second example of the method for evaluating a property of a tumor 55 based on measurement results obtained by the breast measurement apparatus 1A illustrated in FIG. 1 to FIG. 3. As similar to the first example, in the present example, the distance measurement unit 10 measures a distance x1_nc from a skin 51 to a light absorption portion 56 for a normal region with no tumor 55. Further, the light measurement unit 15 measures a normal hemoglobin amount tHb_n in the normal region. This measurement is carried out on normal regions set at a plurality of positions for a plurality of subjects.

Next, as normal correlation data, hemoglobin amount correction data which is correlation data of a correction value is generated, as illustrated by a graph N2 in FIG. 6, based on correlation of the distance x1_nc to the light absorption portion 56 for the normal region and the normal hemoglobin amount tHb_n with reference to measurement data obtained for the plurality of normal regions. This correction data may be prepared as an approximation formula or as a correction table. In the example illustrated in FIG. 6, when a value of the distance x1 is large, the influences of the light absorption portion 56 are regarded to be sufficiently small, and the correction value in that case is set to be 1, and with this value as a reference, the correction correlation data of the correction value for the hemoglobin amount at each distance x1 is obtained.

Subsequently, the distance measurement unit 10 measures a distance x1_tc from the skin 51 to the light absorption portion 56 for an object region with the tumor 55 from a position right above the tumor 55. Further, the light measurement unit 15 measures an object hemoglobin amount tHb_t in the object region from the position right above the tumor 55.

After completing the measurement of the object region, the distance x1_tc to the light absorption portion 56 in the object region is applied to the hemoglobin amount correction data so as to obtain a hemoglobin amount correction value corresponding to the estimate value of the normal hemoglobin amount for the object region. Then, a corrected evaluation value in which the measured object hemoglobin amount tHb_t is corrected is calculated as a property evaluation value of the tumor 55 in the object region based on the obtained correction value. For example, in the case of using the correction data illustrated in FIG. 6, a product of the object hemoglobin amount and the correction value (correction coefficient) is regarded as the corrected evaluation value.

The corrected evaluation value of the hemoglobin amount obtained in this way indicates the total hemoglobin amount on which the influences of the light absorption portion 56 such as the muscle of the chest wall in the object region are reduced. Therefore, it is possible to exactly evaluate the tumor 55 in the object region by evaluating the property of the tumor with the corrected evaluation value as the property evaluation value. In this example, the correction data is prepared in advance as the normal correlation data, however, usual normal correlation data may be prepared so as to correct the object hemoglobin amount based on the estimate value of the normal hemoglobin amount for the object region obtained from the normal correlation data.

(a) and (b) in FIG. 7 are views illustrating a third example of the method for evaluating a property of a tumor 55 based on measurement results obtained by the breast measurement apparatus 1A illustrated in FIG. 1 to FIG. 3. In the above-described first example, the difference value ΔtHb_tn is obtained as the property evaluation value for the tumor 55 by using the measurement results of the distance x1 from the skin 51 to the light absorption portion 56 and the total hemoglobin amount tHb for the normal region and the object region. In contrast, a single or a plurality of evaluation parameters for the tumor 55 may be additionally acquired in addition to the difference value of the hemoglobin amount so as to evaluate the tumor 55 based on the property evaluation value and the additional evaluation parameters.

In the present example, processes to calculation of the difference value ΔtHb_t–tn are similar to those in the first example. Subsequently, a distance x2_t (see FIG. 4) from the skin 51 to the tumor 55 and a tumor diameter r are acquired base on ultrasonic measurement data obtained by the distance measurement unit 10. This measurement is carried out on a plurality of subjects (patients) each having a typical tumor 55 so as to acquire measurement data of the difference value, the distance to the tumor, and the tumor diameter for each subject.

Then, as illustrated in (a) in FIG. 7, for example, coordinate axes are set so that the distance x2_t to the tumor is taken along the x axis, the tumor diameter r is taken along the y axis, and the difference value ΔtHb_t–tn is taken along the z axis, and a graph is drawn by the measurement values so as to analyze the measurement results and to derive a tumor property determination plane N3. This tumor property determination plane N3 is prepared, for example, as an approximation formula or the like represented by the following Formula (4).

$$z = a2 \times x + b2 \times y + d2 \quad (4)$$

Here, the tumor property determination plane N3 may be flat or curved.

Subsequently, the distance measurement unit 10 measures a distance x1_p to the light absorption portion 56 for an object region of the subject including the tumor 55. Further, the light measurement unit 15 measures an object hemoglobin amount tHb_p in the object region. Then, an estimate value tHb_pn of a normal hemoglobin amount for the object region is obtained, and a difference value ΔtHb_p–pn is calculated by the following Formula (5).

$$\Delta tHb\_p-pn = tHb\_p - tHb\_pn \quad (5)$$

$$= tHb\_p - \left\{ \begin{array}{l} a1 \times (x1\_p)^3 + \\ b1 \times (x1\_p)^2 + \\ c1 \times (x1\_p) + d1 \end{array} \right\}$$

Further, the distance measurement unit 10 measures a distance x2_p to the tumor and a tumor diameter r_p so as to plot a measurement data point P3 as illustrated in (b) in FIG. 7. Then, a distance D from the tumor property determination plane N3 to the measurement data point P3 is calculated, and by regarding this as the property evaluation value, the property of the tumor 55 in the object region is evaluated.

In this configuration, the additional evaluation parameter for the tumor 55 is not limited to the above-described distance to the tumor 55 and the tumor diameter r, but various parameters are applicable for the evaluation parameter. For example, regarding the tumor diameter r, as illustrated in (a) and (b) in FIG. 8, more specifically, with respect to a measurement plane defined by the light input unit 16 and the light output unit 17 disposed on the measurement region 50, a vertical diameter (thickness) of the tumor 55 is represented by a, a horizontal diameter parallel to the measurement plane is represented by b, and a horizontal diameter perpendicular to the measurement plane is represented by c, and herein, (1) thickness a, (2) thickness a×horizontal diameter b, (3) thickness a×horizontal diameter c, and (4) product of the diameters in three directions a×b×c and the like can be applied as the evaluation parameter.

Further, regarding the distance to the tumor 55, for example, (1) a distance from the skin to the surface of the tumor, (2) a distance from the skin to the center of the tumor, (3) a distance from the skin to the posterior border of the tumor, and the like can be applied as the evaluation parameter. Further, in the case where the tumor 55 in the object region is small, for example, a thickness of a mammary gland 53, a distance from the skin 51 to the mammary gland 53, and the like can be applied as the evaluation parameter.

The hemoglobin amount acquired by the light measurement unit 15 is not limited to the total hemoglobin amount tHb, and a configuration of acquiring an oxygenated hemoglobin amount $HbO_2$ or a deoxygenated hemoglobin amount Hb, for example, is also applicable. Further, properties of substances such as water, fat, collagen may be acquired by the light measurement unit 15. Further, optical parameters such as an absorption coefficient, an equivalent scattering coefficient, and a refractive index may also be acquired.

The normal correlation data used for evaluating the property of the tumor 55 in the breast measurement apparatus 1A illustrated in FIG. 1 to FIG. 3 will be further described. In the above-described embodiment, regarding the normal correlation data generated based on the measurement results of the distance to the light absorption portion 56 and the hemoglobin amount for the plurality of normal regions of the breast including no tumor 55, single correlation data is prepared, however, a plurality of normal correlation data may be prepared as the normal correlation data in the correlation data storage unit 33 in accordance with attributes of the normal regions.

In the case where the plurality of normal correlation data are prepared, regarding selection of the normal correlation data used for calculating the evaluation value, the normal correlation data used for deriving the estimate value of the normal hemoglobin amount for the object region may be selected based on an attribute of the object region, in the evaluation value calculation process by the evaluation value calculation unit 35. Alternatively, the normal correlation data used for deriving the estimate value of the normal hemoglobin amount for the object region may be selected based on the measurement result for the normal region set on the subject of the object region, in the evaluation value calculation process by the evaluation value calculation unit 35.

In this way, by properly selecting the single normal correlation data by a predetermined selection method from the plurality of normal correlation data prepared in accordance with the attributes of the normal regions and stored in the correlation data storage unit 33, and by applying the selected normal correlation data so as to derive the estimate value of the normal hemoglobin amount for the object region and to calculate the property evaluation value of the tumor 55 in the object region, it is possible to further improve the measurement accuracy of the property of the tumor 55 inside the breast.

Further, in the case of using the plurality of normal correlation data as described above, specifically, the plurality of normal correlation data may be prepared in the correlation data storage unit 33 in accordance with ages of the subjects or menopause states of the subjects which are the attributes of the normal regions. In general, an attribute of the measurement region itself or an attribute of a subject of the measurement region or the like can be used as the attribute of the measurement region which is referred to in generating and selecting the normal correlation data.

Further, regarding the normal correlation data, the correlation data storage unit 33 may be configured to prepare correlation data generated based on the measurement results for the plurality of normal regions set on the subject of the object region as the normal correlation data. According to this configuration, the normal correlation data applied to the measurement result of the object region including the tumor 55 can be preferably set in accordance with the subject having the object region.

Alternatively, regarding the normal correlation data, the evaluation value calculation unit 35 may correct the normal correlation data used for deriving the estimate value of the normal hemoglobin amount for the object region based on the measurement results for the single or the plurality of normal regions set on the subject of the object region. According to this configuration, the normal correlation data applied to the measurement result of the object region can be preferably set in accordance with the subject having the object region.

Figure 9:
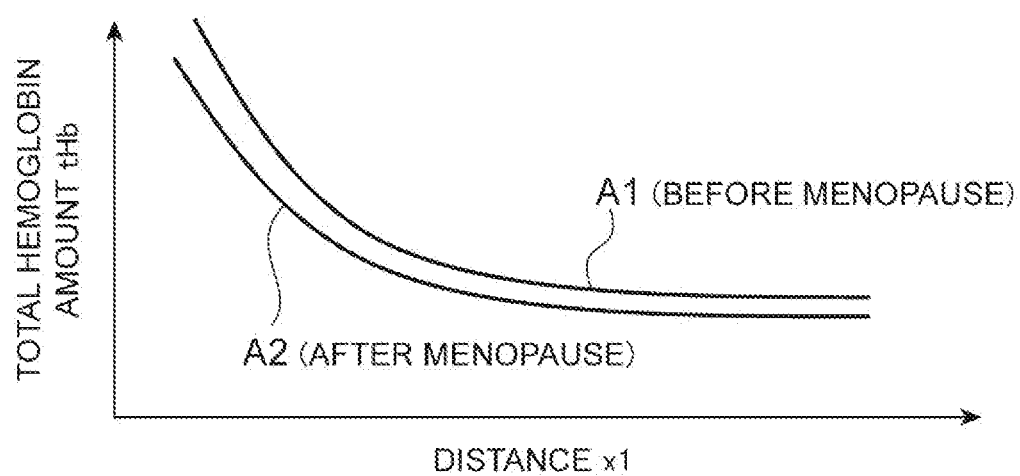
FIG. 9 is a graph illustrating a plurality of normal correlation data prepared in accordance with menopause states of subjects.

FIG. 9 is a graph illustrating a plurality of normal correlation data prepared in accordance with the menopause states of subjects, taking the menopause state of the subject into consideration as the attribute of the measurement region (normal region, object region) in the subject. In FIG. 9, a graph A1 indicates normal correlation data for the normal region of the subject before menopause, whereas a graph A2 indicates normal correlation data for the normal region of the subject after menopause.

As illustrated in FIG. 9, the correlation of the distance x1 to the light absorption portion 56 and the hemoglobin amount tHb changes depending on the menopause state of the subject, before menopause or after menopause. Therefore, by preparing a plurality of normal correlation data A1 and A2 in the correlation data storage unit 33, and selecting the normal correlation data in the evaluation value calculation unit 35 based on the menopause state of the subject of the object region including the tumor 55 or the like input from the input device 39 by the operator, it is possible to improve the measurement accuracy of the property of the tumor 55. FIG. 9 illustrates a configuration of preparing the normal correlation data before and after menopause, however, a configuration of preparing, for example, normal correlation data before and after chemotherapy may also be applicable.

Figure 10:
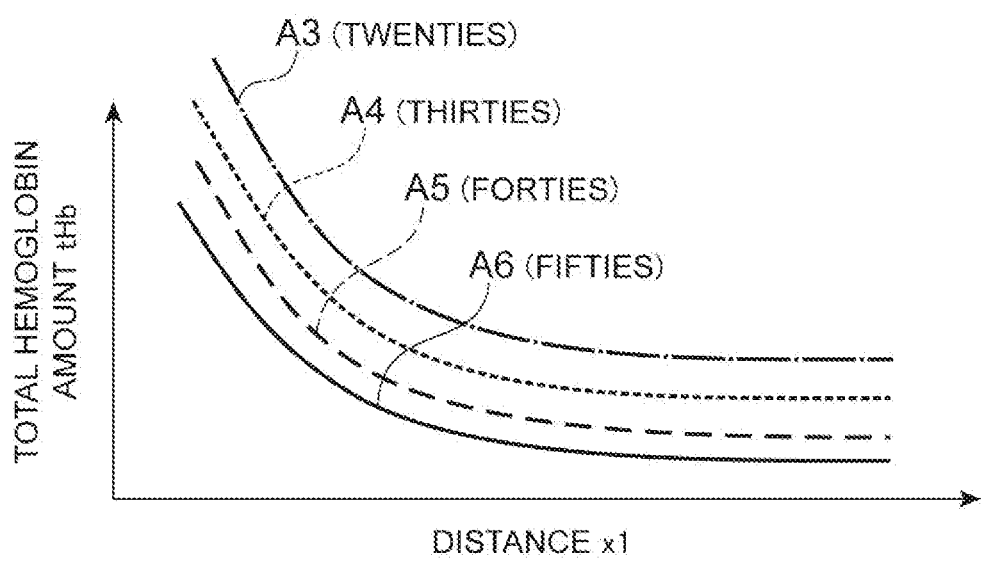
FIG. 10 is a graph illustrating a plurality of normal correlation data prepared in accordance with ages of subjects.

FIG. 10 is a graph illustrating a plurality of normal correlation data prepared in accordance with ages of subjects, taking the age of the subject into consideration as the attribute of the measurement region (normal region, object region) in the subject. In FIG. 10, a graph A3 indicates normal correlation data for the subjects of twenties, a graph A4 indicates normal correlation data for the subjects of thirties, a graph A5 indicates normal correlation data for the subjects of forties, and a graph A6 indicates normal correlation data for the subjects of fifties.

As illustrated in FIG. 10, the correlation of the distance x1 to the light absorption portion 56 and the hemoglobin amount tHb changes depending on the age of the subject, twenties, thirties, forties, or fifties, as similar to the menopause state. Therefore, by preparing a plurality of normal correlation data A3 to A6 in the correlation data storage unit 33, and selecting the normal correlation data in the evaluation value calculation unit 35 based on the age of the subject of the object region including the tumor 55 or the like input from the input device 39 by the operator, it is possible to improve the measurement accuracy of the property of the tumor 55.

As FIG. 9 and FIG. 10 illustrate examples for the menopause states and ages of the subjects, in the case where the plurality of normal correlation data are prepared in accordance with attributes of the normal regions, as described above, the normal correlation data may be selected in the evaluation value calculation unit 35 based on the corresponding attribute (for example, menopause state, age, or the like) of the object region. Alternatively, other than such a configuration, without considering the attribute of the object region directly, the normal correlation data may be selected based on a measurement result for a normal region set on a subject of an object region as illustrated in FIG. 11.

Figure 11:
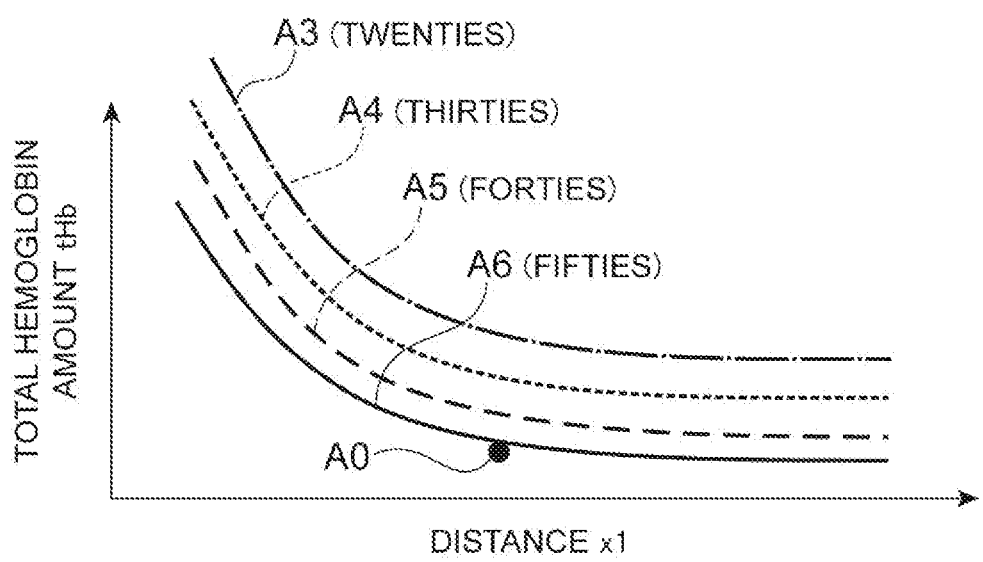
FIG. 11 is a graph illustrating selection of the normal correlation data based on the measurement result for the normal region set on the subject of the object region.

In an example illustrated in FIG. 11, for the normal correlation data A3 to A6 of the twenties to fifties prepared as similar to FIG. 10, in the case where the actual age of the subject of the object region including the tumor 55 is in thirties, the normal correlation data A4 corresponding to the thirties will not be selected, instead, the normal region is set at a position other than the object region for the subject of the object region, and with reference to a measurement data point A0 illustrated in FIG. 11 which is the measurement result for the normal region, the normal correlation data A6 of the fifties which is the closest to the measurement data point A0 is selected as the normal correlation data to be applied to the subject. According to such a method, it is possible to improve the measurement accuracy of the property of the tumor 55.

Here, regarding setting of the normal region in the subject of the object region including the tumor 55, specifically, for example, when the tumor 55 is included in one breast of the subject, a method of setting the normal region on the other breast with no tumor 55 and carrying out measurement may be used. Alternatively, a method of setting a region with no tumor 55 within the one breast including the tumor 55 as the normal region may be used.

Figure 12:
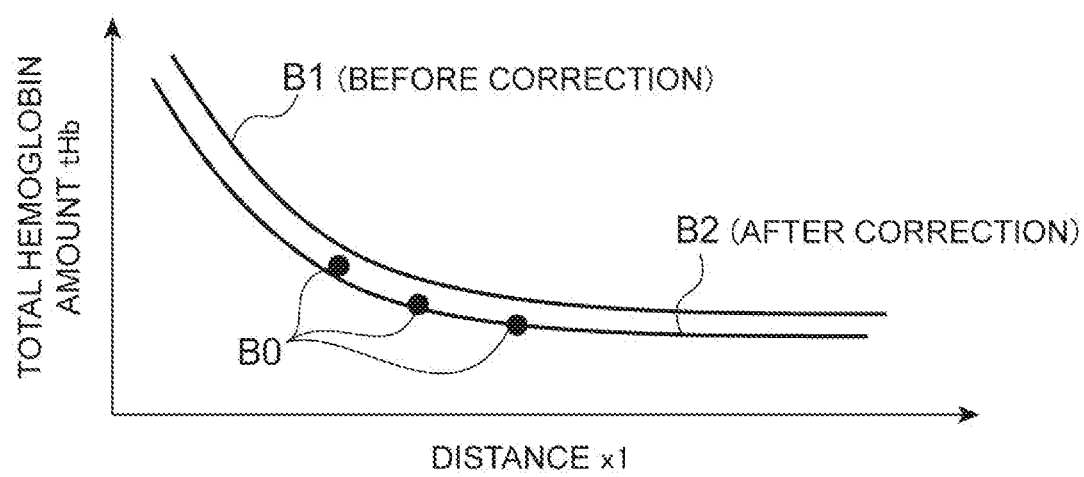
FIG. 12 is a graph illustrating correction of the normal correlation data based on the measurement result for the normal region set on the subject of the object region.

FIG. 12 is a graph illustrating correction of the normal correlation data based on measurement results for normal regions set on the subject of the object region. In an example illustrated in FIG. 12, the normal regions on the subject of the object region are set for normal correlation data B1 before correction prepared in the correlation data storage unit 33. Then, the evaluation value calculation unit 35 corrects the correlation data based on measurement data points B0 which are the measurement results for the normal regions so as to apply corrected normal correlation data B2 to the calculation of the property evaluation value.

The normal regions set herein on the subject of the object region may be single or plural. FIG. 12 indicates the measurement data points B0 in the case where three normal regions are set. Further, regarding the measurement result for the normal region, correction may be performed by using a previously acquired measurement result for the normal region of the subject.

Figure 13:
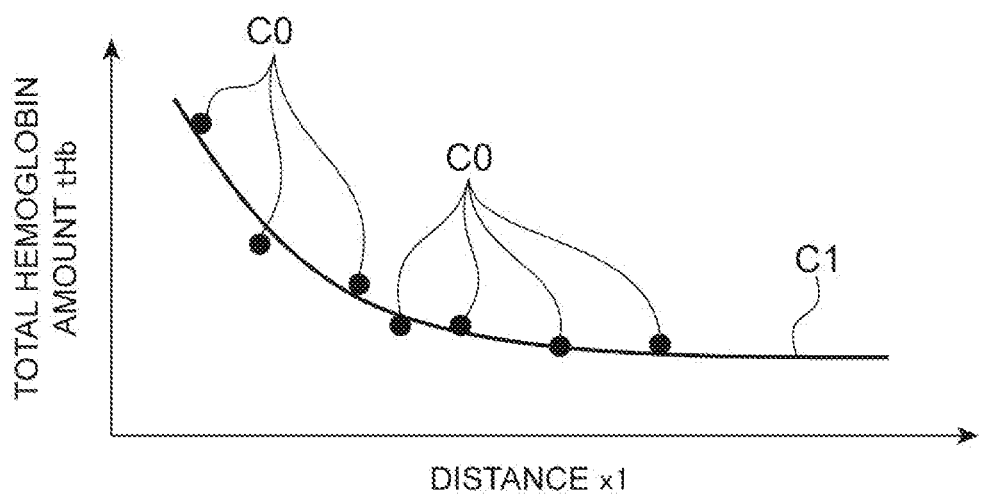
FIG. 13 is a graph illustrating the normal correlation data generated from the measurement results for the plurality of normal regions set on the subject of the object region.

FIG. 13 is a graph illustrating normal correlation data generated based on measurement results for a plurality of normal regions set on the subject of the object region. In an example illustrated in FIG. 13, the plurality of normal regions on the subject of the object region are set so as to acquire a plurality of measurement data points C0 of measurement results. Then, normal correlation data C1 is generated based on correlation in the plurality of measurement data points C0 and is stored in the correlation data storage unit 33.

Here, property evaluation of the tumor 55 carried out by the breast measurement apparatus 1A of the embodiment is considered to be an effective method, for example, in the case of observing an effect of the chemotherapy in the long term or of performing follow-up observation of an effect of an anticancer drug treatment for the subject having the tumor 55 inside the breast. In such a case, as illustrated in FIG. 13, it is important to perform measurement at a plurality of positions for normal portions of the subject to be measured and to prepare normal correlation data for the subject.

The breast measurement method and breast measurement apparatus according to the present invention do not have to be limited to the above-described embodiment and configuration examples, but can be modified in various ways. For example, in the above embodiment, the ultrasonic measurement method is used as the predetermined distance measurement method for acquiring the distance to the light absorption portion, however, it is not limited to such a configuration, and for example, the method and apparatus may include a configuration in which the distance to the light absorption portion is measured by an optical CT measurement method or the like which is one of the light measurement method.

Regarding the light measurement method for acquiring the hemoglobin amount in the measurement region, the time resolved spectroscopy (TRS) is used in the above embodiment, however, it is not limited to such a configuration, and for example, a phase modulation spectroscopy (PMS) utilizing modulation light or a method using CW light as the measurement light or the like may also be used to measure the hemoglobin amount. Further, in the case where the measurement region 50 includes a nipple, a thickness of the nipple may be taken into consideration.

Regarding the measurement probe 18 in the breast measurement apparatus 1A, a configuration of a multi-channel combining the plurality of light input units 16 and the plurality of light output units 17 is illustrated in FIG. 1, however, it is not limited to such a configuration, and specifically, measurement probes with various configurations may also be used. For example, a modification example of the measurement probe 18 illustrated in FIG. 14 includes a configuration of one channel combining a single light input unit 16 and a single light output unit 17. In such a one-channel measurement probe, the measurement light having different wavelengths is input from the light input unit 16 to the measurement region 50 in time series. Further, arrangement of the light input unit 16 and the light output unit 17 with respect to the ultrasonic measurement unit 11 is not limited to the configuration examples illustrated in FIG. 1 and FIG. 14, but the arrangement can be modified to various configurations.

The breast measurement method according to the above embodiment is configured as a breast measurement method for measuring a property of a tumor inside a breast of a measurement object, (1) by using a predetermined measurement method of measuring, for a light absorption portion set inside a breast as a distance measurement object, a distance from a skin to the light absorption portion for a measurement region which is a normal region of the breast including no tumor or an object region of the breast including a tumor, and a light measurement method of inputting measurement light into the measurement region through a light input unit, detecting output light output through a light output unit, and measuring a hemoglobin amount in the measurement region, the method including: (2) a correlation data acquisition step of acquiring normal correlation data of the distance to the light absorption portion and a normal hemoglobin amount generated by acquiring the distance to the light absorption portion for each of a plurality of normal regions by the predetermined measurement method and acquiring the normal hemoglobin amount in the normal region by the light measurement method; (3) an object data acquisition step of acquiring the distance to the light absorption portion for the object region by the predetermined measurement method and acquiring an object hemoglobin amount in the object region by the light measurement method; and (4) an evaluation value calculation step of calculating a property evaluation value of the tumor inside the object region based on the normal hemoglobin amount, obtained from the normal correlation data and the distance to the light absorption portion in the object region, and the object hemoglobin amount in the object region.

Further, the breast measurement apparatus according to the above embodiment is configured as a breast measurement apparatus for measuring a property of a tumor inside a breast of a measurement object, the apparatus including: (a) a distance measurement unit for measuring, for a light absorption portion set inside a breast as a distance measurement object, a distance from a skin to the light absorption portion for a measurement region which is a normal region of the breast including no tumor or an object region of the breast including a tumor by a predetermined measurement method; (b) a light measurement unit, including a light source device for inputting measurement light into the measurement region through a light input unit and a light detection device for detecting output light output from the measurement region through a light output unit, for measuring a hemoglobin amount in the measurement region by a light measurement method; (c) a correlation data storage unit for storing normal correlation data of the distance to the light absorption portion and a normal hemoglobin amount generated by acquiring the distance to the light absorption portion for each of a plurality of normal regions by the distance measurement unit and acquiring the normal hemoglobin amount in the normal region by the light measurement unit; and (d) an evaluation value calculation unit for calculating a property evaluation value of the tumor inside the object region based on the normal hemoglobin amount, obtained from the normal correlation data and the distance to the light absorption portion in the object region acquired by the distance measurement unit, and an object hemoglobin amount in the object region acquired by the light measurement unit.

In the breast measurement method and measurement apparatus of the above-described configuration, the hemoglobin amount in the measurement region acquired by the light measurement method is, for example, a total hemoglobin amount. Alternatively, an oxygenated hemoglobin amount or a deoxygenated hemoglobin amount may be acquired as the hemoglobin amount. In general, at least one of the oxygenated hemoglobin amount, the deoxygenated hemoglobin amount, and the total hemoglobin amount may be acquired as the hemoglobin amount.

Here, regarding the normal correlation data acquired for the normal regions of the breast including no tumor, in the breast measurement method, preferably, in the correlation data acquisition step, a plurality of normal correlation data are prepared in accordance with attributes of the normal regions as the normal correlation data, and in the evaluation value calculation step, the normal correlation data used for deriving the normal hemoglobin amount is selected based on the attribute of the object region. Similarly, in the breast measurement apparatus, preferably, the correlation data storage unit prepares a plurality of normal correlation data in accordance with attributes of the normal regions as the normal correlation data, and the evaluation value calculation unit selects the normal correlation data used for deriving the normal hemoglobin amount based on the attribute of the object region.

Alternatively, regarding the normal correlation data, in the breast measurement method, in the correlation data acquisition step, a plurality of normal correlation data may be prepared in accordance with attributes of the normal regions as the normal correlation data, and in the evaluation value calculation step, the normal correlation data used for deriving the normal hemoglobin amount may be selected based on a measurement result for the normal region set on a subject of the object region. Similarly, in the breast measurement apparatus, the correlation data storage unit may prepare a plurality of normal correlation data in accordance with attributes of the normal regions as the normal correlation data, and the evaluation value calculation unit may select the normal correlation data used for deriving the normal hemoglobin amount based on a measurement result for the normal region set on a subject of the object region.

In this way, by properly selecting single normal correlation data from the plurality of normal correlation data prepared in accordance with attributes of the normal regions by the predetermined selection method, and by applying the selected normal correlation data so as to derive the estimate value of the normal hemoglobin amount in the object region and to calculate the property evaluation value of the tumor in the object region, it is possible to further improve the measurement accuracy of the property of the tumor inside the breast.

Further, in the case of using the plurality of normal correlation data as described above, specifically, in the breast measurement method, in the correlation data acquisition step, the plurality of normal correlation data may be prepared in accordance with ages or menopause states of the subjects which are the attributes of the normal regions. Similarly, in the breast measurement apparatus, the correlation data storage unit may prepare the plurality of normal correlation data in accordance with ages or menopause states of the subjects which are the attributes of the normal regions. In general, the attribute of the measurement region itself or the attribute of the subject of the measurement region or the like can be used as the attribute of the measurement region which is referred to in generating or selecting the normal correlation data.

Further, in the breast measurement method, in the correlation data acquisition step, correlation data generated based on the measurement results for the plurality of normal regions set on the subject of the object region may be prepared as the normal correlation data. Similarly, in the breast measurement apparatus, the correlation data storage unit may prepare correlation data generated based on the measurement results for the plurality of normal regions set on the subject of the object region as the normal correlation data. According to this configuration, the normal correlation data applied to the measurement result of the object region including the tumor can be preferably set in accordance with the subject having the object region.

Alternatively, in the breast measurement method, in the evaluation value calculation step, the normal correlation data used for deriving the normal hemoglobin amount may be corrected based on the measurement result for the normal region set on the subject of the object region. Similarly, in the breast measurement apparatus, the evaluation value calculation unit may correct the normal correlation data used for deriving the normal hemoglobin amount based on the measurement result for the normal region set on the subject of the object region. According to this configuration, the normal correlation data applied to the measurement result of the object region including the tumor can be preferably set in accordance with the subject having the object region.

Further, in the breast measurement method, preferably, the predetermined measurement method for measuring the distance to the light absorption portion is an ultrasonic measurement method of acquiring ultrasonic measurement data of the measurement region by transmitting ultrasonic wave to the measurement region and receiving reflected ultrasonic wave. Similarly, in the breast measurement apparatus, preferably, the predetermined measurement method for measuring the distance to the light absorption portion in the distance measurement unit is an ultrasonic measurement method of acquiring ultrasonic measurement data of the measurement region by transmitting ultrasonic wave to the measurement region and receiving reflected ultrasonic wave. In this way, the distance to the light absorption portion can be preferably measured by using the ultrasonic measurement method as the measurement method for measuring the distance from the skin to the light absorption portion in the measurement region.

Regarding the property evaluation value of the tumor, specifically, in the breast measurement method, in the evaluation value calculation step, a difference value between the normal hemoglobin amount and the object hemoglobin amount obtained for the object region may be calculated as the property evaluation value. Similarly, in the breast measurement apparatus, the evaluation value calculation unit may calculate a difference value between the normal hemoglobin amount and the object hemoglobin amount obtained for the object region as the property evaluation value.

Alternatively, in the breast measurement method, in the evaluation value calculation step, a corrected evaluation value in which the object hemoglobin amount is corrected based on the normal hemoglobin amount obtained for the object region may be calculated as the property evaluation value. Similarly, in the breast measurement apparatus, the evaluation value calculation unit may calculate a corrected evaluation value in which the object hemoglobin amount is corrected based on the normal hemoglobin amount obtained for the object region as the property evaluation value.

In this way, according to the configuration in which the difference value of the hemoglobin amounts or the corrected evaluation value of the hemoglobin amount is used as the property evaluation value for the tumor in the object region, it is possible to preferably evaluate and determine the property of the tumor based on the measurement result.

Further, in the breast measurement method, in the correlation data acquisition step, hemoglobin amount correction data generated based on correlation of the distance to the light absorption portion and the normal hemoglobin amount may be prepared as the normal correlation data, and in the evaluation value calculation step, a corrected evaluation value in which the object hemoglobin amount is corrected based on a correction value obtained from the hemoglobin amount correction data and the distance to the light absorption portion in the object region may be calculated as the property evaluation value. Similarly, in the breast measurement apparatus, the correlation data storage unit may prepare hemoglobin amount correction data generated based on correlation of the distance to the light absorption portion and the normal hemoglobin amount as the normal correlation data, and the evaluation value calculation unit may calculate a corrected evaluation value in which the object hemoglobin amount is corrected based on a correction value obtained from the hemoglobin amount correction data and the distance to the light absorption portion in the object region as the property evaluation value.

In this way, according to the configuration of preparing the hemoglobin amount correction data used for correcting the object hemoglobin amount as the normal correlation data, it is possible to preferably evaluate and determine the property of the tumor based on the measurement result.

Regarding the light absorption portion which absorbs the measurement light of the predetermined wavelength at a certain level or more and influences on the measurement result in the light measurement inside the breast and which is set as the distance measurement object, specifically, the light absorption portion set inside the breast is preferably a muscle of a chest wall, a rib, a mammary gland, or a lung. It is possible to preferably improve the measurement accuracy of the property of the tumor inside the breast by taking into consideration the influences on the measurement result of the light absorption in these portions. The light absorption portion is preferably properly set as taking into consideration the light absorption property and the like in the portion inside the breast or the vicinal portion thereof.

Further, in the breast measurement method, in the evaluation value calculation step, a single or a plurality of evaluation parameters for the tumor may be acquired in addition to the property evaluation value, and the property of the tumor may be evaluated based on the property evaluation value and the single or the plurality of evaluation parameters. Similarly, in the breast measurement apparatus, the evaluation value calculation unit may acquire a single or a plurality of evaluation parameters for the tumor in addition to the property evaluation value, and may evaluate the property of the tumor based on the property evaluation value and the single or the plurality of evaluation parameters. According to this configuration, it is possible to further improve the measurement accuracy of the property of the tumor inside the breast.

INDUSTRIAL APPLICABILITY

The present invention can be used as a breast measurement method and a breast measurement apparatus capable of improving measurement accuracy of a property of a tumor inside a breast.

REFERENCE SIGNS LIST

1A—breast measurement apparatus, 10—distance measurement unit, 11—ultrasonic measurement unit, 15—light measurement unit, 16—light input unit, 17—light output unit, 18—measurement probe, 20—light source device, 25—light detection device, 30—measurement processing device, 31—distance measurement processing unit, 32—light measurement processing unit, 33—correlation data storage unit, 34—correlation data generation unit, 35—evaluation value calculation unit, 36—tumor property evaluation unit, 38—display device, 39—input device,
50—measurement region (normal region, object region), 51—skin, 52—fat, 53—mammary gland, 55—tumor, 56—light absorption portion, 58—propagation path area.

The invention claimed is:

1. A breast measurement method for measuring a property of a tumor inside a breast of a measurement object, the method comprising:
measuring, for a light absorption portion set inside a breast as a distance measurement object, a distance from a skin to the light absorption portion for a plurality of measurement regions, wherein the plurality of measurement regions include a plurality of normal regions of the breast including no tumor, and at least one object region of the breast including a tumor, and wherein the distance to the light absorption portion is measured using ultrasonic measurement;
inputting measurement light into each of the plurality of measurement regions through a light input probe;
detecting output light output through a light output probe based on the inputted measurement light;
measuring a hemoglobin amount in each of the plurality of measurement regions based on the detected output light;
acquiring normal correlation data of the distance to the light absorption portion and a normal hemoglobin amount generated by acquiring the distance to the light absorption portion for each of the plurality of normal regions;
acquiring the normal hemoglobin amount in the plurality of normal regions based on the normal correlation data and the distance to the light absorption portion in the at least one object region;
acquiring an object hemoglobin amount in the at least one object region based on the measured hemoglobin amount in the plurality of measurement regions; and
calculating a property evaluation value of the tumor inside the at least one object region based on the normal hemoglobin amount, obtained from the normal correlation data and the distance to the light absorption portion in the at least one object region, and the object hemoglobin amount in the at least one object region.

2. The breast measurement method according to claim 1, wherein acquiring normal correlation data of the distance to the light absorption portion and the normal hemoglobin amount generated by acquiring the distance to the light absorption portion for each of the plurality of normal regions includes:
preparing a plurality of normal correlation data in accordance with attributes of the plurality of normal regions as the normal correlation data,
wherein calculating the property evaluation value of the tumor inside the at least one object region includes:
selecting the normal correlation data used for deriving the normal hemoglobin amount based on an attribute of the at least one object region.

3. The breast measurement method according to claim 1, wherein acquiring normal correlation data of the distance to the light absorption portion and the normal hemoglobin amount generated by acquiring the distance to the light absorption portion for each of the plurality of normal regions includes:
preparing a plurality of normal correlation data in accordance with attributes of the plurality of normal regions as the normal correlation data, and
wherein calculating the property evaluation value of the tumor inside the at least one object region includes:
selecting the normal correlation data used for deriving the normal hemoglobin amount based on a measurement result for the plurality of normal regions set on a subject of the at least one object region.

4. The breast measurement method according to claim 1, wherein the distance to the light absorption portion is measured using ultrasonic measurement to acquire ultrasonic measurement data of the plurality of measurement regions by at least one transmitting ultrasonic wave to the plurality of measurement regions and receiving at least one reflected ultrasonic wave.

5. The breast measurement method according to claim 1, wherein calculating the property evaluation value of the tumor inside the at least one object region includes:
calculating, as the property evaluation value, a difference value between the normal hemoglobin amount and the object hemoglobin amount obtained for the at least one object region.

6. The breast measurement method according to claim 1, wherein the light absorption portion set inside the breast is a muscle of a chest wall, a rib, a mammary gland, or a lung.

7. The breast measurement method according to claim 1, wherein calculating the property evaluation value of the tumor inside the at least one object region includes:
acquiring a single or a plurality of evaluation parameters for the tumor in addition to the property evaluation value; and
evaluating the property of the tumor based on the property evaluation value and the single or the plurality of evaluation parameters.

8. A breast measurement apparatus for measuring a property of a tumor inside a breast of a measurement object, the apparatus comprising a computer configured to execute a method comprising:
receiving a measurement, for a light absorption portion set inside a breast as a distance measurement object, of a distance from a skin to the light absorption portion for a plurality of measurement regions, wherein the plurality of measurement regions includes a plurality of normal regions of the breast including no tumor, and at least one object region of the breast including a tumor, and wherein the distance to the light absorption portion is measured using ultrasonic measurement;
receiving a measurement of a hemoglobin amount in each of the plurality of measurement regions, the measurement of the hemoglobin amount in the plurality of measurement regions measured based on measurement light inputted into the plurality of measurement regions through a light input probe and output light detected through a light output probe receiving the inputted measurement light;

acquiring normal correlation data of the distance to the light absorption portion and a normal hemoglobin amount generated by acquiring the distance to the light absorption portion for each of the plurality of normal regions;

acquiring the normal hemoglobin amount in the plurality of normal regions based on the normal correlation data and the distance to the light absorption portion in the at least one object region;

acquiring an object hemoglobin amount in the at least one object region based on the measured hemoglobin amount in the plurality of measurement regions; and calculating a property evaluation value of the tumor inside the at least one object region based on the normal hemoglobin amount, obtained from the normal correlation data and the distance to the light absorption portion in the at least one object region, and the object hemoglobin amount in the at least one object region.

9. The breast measurement apparatus according to claim 8,
wherein acquiring normal correlation data of the distance to the light absorption portion and the normal hemoglobin amount generated by acquiring the distance to the light absorption portion for each of the plurality of normal regions includes:
preparing a plurality of normal correlation data in accordance with attributes of the plurality of normal regions as the normal correlation data, and
wherein calculating the property evaluation value of the tumor inside the at least one object region includes:
selecting the normal correlation data used for deriving the normal hemoglobin amount based on an attribute of the at least one object region.

10. The breast measurement apparatus according to claim 8,
wherein acquiring normal correlation data of the distance to the light absorption portion and the normal hemoglobin amount generated by acquiring the distance to the light absorption portion for each of the plurality of normal regions includes:
preparing a plurality of normal correlation data in accordance with attributes of the plurality of normal regions as the normal correlation data, and
wherein calculating the property evaluation value of the tumor inside the at least one object region includes:
selecting the normal correlation data used for deriving the normal hemoglobin amount based on a measurement result for the plurality of normal regions set on a subject of the at least one object region.

11. The breast measurement apparatus according to claim 8, wherein the distance to the light absorption portion is measured using ultrasonic measurement to acquire ultrasonic measurement data of the plurality of measurement regions by at least one transmitting ultrasonic wave to the plurality of measurement regions and receiving at least one reflected ultrasonic wave.

12. The breast measurement apparatus according to claim 8, wherein calculating the property evaluation value of the tumor inside the at least one object region includes:
calculating, as the property evaluation value, a difference value between the normal hemoglobin amount and the object hemoglobin amount obtained for the at least one object region.

13. The breast measurement apparatus according to claim 8, wherein the light absorption portion set inside the breast is a muscle of a chest wall, a rib, a mammary gland, or a lung.

14. The breast measurement apparatus according to claim 8, wherein calculating the property evaluation value of the tumor inside the at least one object region includes:
acquiring a single or a plurality of evaluation parameters for the tumor in addition to the property evaluation value; and
evaluating the property of the tumor based on the property evaluation value and the single or the plurality of evaluation parameters.

* * * * *